US00PP12800P2

(12) United States Plant Patent
Spivey

(10) Patent No.: US PP12,800 P2
(45) Date of Patent: Jul. 23, 2002

(54) ANTIGONON PLANT NAMED 'COLVEY'

(75) Inventor: James W. Spivey, Devine, TX (US)

(73) Assignee: Color Spot Nurseries, Inc., San Antonio, TX (US)

( * ) Notice: Subject to any disclaimer, the term of this patent is extended or adjusted under 35 U.S.C. 154(b) by 39 days.

(21) Appl. No.: 09/774,366

(22) Filed: Feb. 1, 2001

(51) Int. Cl.[7] ..... A01H 5/00

(52) U.S. Cl. ..... Plt./226
(58) Field of Search ..... Plt./226

*Primary Examiner*—Bruce R. Campell
*Assistant Examiner*—Michelle Kizilkaya
(74) *Attorney, Agent, or Firm*—C. A. Whealy

(57) ABSTRACT

A distinct cultivar of Antigonon plant named 'Colvey', characterized by its large dark reddish pink-colored flowers; freely flowering habit with flowering racemes developing at every node; relatively early flowering; and tolerance to high temperatures.

1 Drawing Sheet

BACKGROUND OF THE INVENTION

The present Invention relates to a new and distinct cultivar of Antigonon plant, botanically known as *Antigonon leptopus*, and hereinafter referred to by the name 'Colvey'.

The new Antigonon was discovered by the Inventor in 1997 in a controlled environment in Fredericksburg, Tex., as a seedling of random cross pollinations of unidentified selections of *Antigonon leptopus*, not patented. The new Antigonon was selected by the Inventor on the basis of its larger and darker pink-colored flowers compared to the unidentified selections of *Antigonon leptopus*.

Asexual reproduction of the new cultivar by terminal cuttings taken in San Antonio, Tex. has shown that the unique features of this new Antigonon are stable and reproduced true to type in successive generations.

SUMMARY OF THE INVENTION

Plants of the cultivar Colvey have not been observed under all possible environmental conditions. The phenotype may vary somewhat with variations in environment such as temperature, light intensity, daylength, irrigation frequency and rate, and/or fertilizer type and rate without, however, any variance in genotype.

The following traits have been repeatedly observed and are determined to be the unique characeristics of 'Colvey'. These charqacteristics in combination distinguish 'Colvey' as a new and distinct cultivar:

1. Large dark reddish pink-colored flowers.

2. Freely flowering with flowering racemes developing at every node.

3. Relatively early flowering.

4. Tolerant to high temperatures.

The new Antigonon can be compared to plants of the *Antigonon leptopus* cultivar Sunset Rose, not patented. In side-by-side comparisions conducted by the Inventor in San Antonio, Tex., plants of the new Antigonon have larger flowers and darker pink-colored flowers than plants of the cultivar Sunset Rose. In addition, plants of the new Antigonon flower about one to two weeks earlier than plants of the cultivar Sunset Rose.

BRIEF DESCRIPTION OF THE PHOTOGRAPHS

The accopanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new Antigonon.

The photograph at the top of the sheet comprises a top perspective view of a lateral branch of a typical plants of 'Colvey'.

The photograph at the bottom of the sheet comprises a close-up view of typical flowers and leaves of 'Colvey'.

DETAILED BOTANICAL DESCRIPTION

In the following description, color references are made to The Royal Horticultural Society Colour Chart except where general terms of ordinary dictionary significance are used. Plants grown in one-gallon containers for about four to five months after rooting were used for the photographs and the following description. Plants were grown under outdoor nursery conditions which closely approximate commercial production conditions in San Antonio, Tex., during the spring and summer.

Botanical classification: *Antigonon leptopus* cultivar Colvey.

Parentage: Seedling originating from various cross pollinations of unidentified selections of *Antigonon leptopus*, not patented.

Propagation:

*Type cutting.*—Terminal vegetative cuttings.

*Time to initiate roots, summer.*—About 21 to 30 days at temperatures of 29 to 35° C.

*Time to initiate roots, winter.*—About 30 to 60 days at temperatures of 13 to 18° C.

*Time to produce a rooted liner, summer.*—About 60 to 70 days at temperatures of 29 to 35° C.

*Time to produce a rooted liner, winter.*—About 70 to 80 days at temperatures of 13 to 18° C.

*Root description.*—Numerous, fine to thick, and freely branching.

Plant description:

*Form.*—Perennial vine; indeterminate. Flower racemes axillary with terminal tendrils; plants climbing with support; trailing without support. When pinched, about 10 lateral branches develop per plant.

*Plant length.*—About 2 meters.

*Plant diameter.*—About 32 cm.

*Vigor.*—Relatively rapid growth rate and vigorous.

*Lateral branches.*—Length: About 2 meters. Diameter: Thick, about 4 cm. Internode length: About 10.5 cm. Strength: Very strong. Texture: Pubescent; longitudinally ridged. Color: Young stems: Green, 146A, with dark purple, 183A to 183B, overtones on upper surfaces. Mature stems: Green, 148B with brown, 166A to 166B, overtones,

*Foliage description.*—Leaves simple, generally symmetrical and long-persisting; arrangement, alternate. Length: From petiole attachment to apex: About 10.5 cm. From leaf base to apex: About 14.5 cm. Width: About 10.25 cm. Shape: Cordate. Apex: Acute. Base: Cordate, lobes symmetrical. Margin: Entire. Aspect: Folded along midvein. Texture: Flexible; velvety with very fine pubescence on both surfaces. Color: Young foliage, upper surface: Green, 146A. Young foliage, lower surface: Green, 147B. Mature foliage, upper surface: More green than 146A. Mature foliage, lower surface: Green, 147B. Petiole length: About 3.6 cm. Petiole diameter: About 2 mm. Petiole texture: Pubescent. Petiole color: Green, close to 144A to 144B, Flower description:

*Flower type and habit.*—Single flowers arranged in axillary racemes; typically one raceme per node, terminating with a tendril; flowers face outwardly. Flowers not persistent. Very freely flowering, typically about 12 to 20 open flowers and flower buds per raceme.

*Natural flowering season.*—Late spring until frost in the autumn; flowering continuous.

*Flower longevity on the plant.*—Typically less than one week.

*Fragrance.*—Not detectable.

*Raceme size.*—Length: About 13.3 cm. Diameter: About 4.7 cm.

*Flower size.*—Diameter: About 1.5 cm. Depth (height): About 1.3 cm.

*Flower buds* (*showing color*).—Length: About 1 mm. Diameter: About 1 mm. Shape: Spherical. Color: Initially purple, close to 59A, then dark reddish pink, 57A.

*Corona.*—Arrangement/appearance: Single whorl of five sepals, fused at base. Length: About 1.4 cm. Width: About 1.5 cm. Shape: Almost circular. Apex: Rounded, orbicular. Base: Auriculate. Margin: Entire. Texture: Satiny; rugose. Color: Upper surface, when opening and fully opened flower: 57A. Lower surface, when opening and fully opened flower: 57B.

*Peduncles.*—Length: About 13.3 cm. Width: About 1.5 mm. Angle: Erect, approximately at right angles to lateral stem. Strength: Strong. Texture: Very fine reddish pubescence. Color: Close to 144A.

*Pedicels.*—Length: About 1.1 cm. Width: Less than 1 mm. Angle: Erect, approximately at right angles to peduncle. Strength: Strong; flexible. Texture: Very fine reddish pubescence. Color: Close to 57A.

*Tendrils.*—Length: About 1.5 to 15.5 cm. Width: Less than 1 mm. Strength: Very strong; wiry. Texture: Pubescent. Color: Close to 144A.

*Reproductive organs.*—Stamens: Quantity: About six to eight fused into a crown-like structure. Anther shape: Sharply acute and hook-like. Anther length: About 1 mm. Anther color: Close to 14A. Filament color: 57A. Pollen amount: None observed. Pistils: Quantity: One to three. Pistil length: About 3 mm. Stigma color: Light yellow. Ovary color: Close to 154A.

*Seed.*—Seed production has not been observed.

Disease resistance: Plants of the new Antigonon have not been observed to be resistant to pathogens common to Antigonon.

Weather tolerance: Plants of the new Antigonon have been observed to be tolerant to temperatures above 40° C.

It is claimed:

1. A new and distinct cultivar of Antigonon plant named 'Colvey', as illustrated and described.

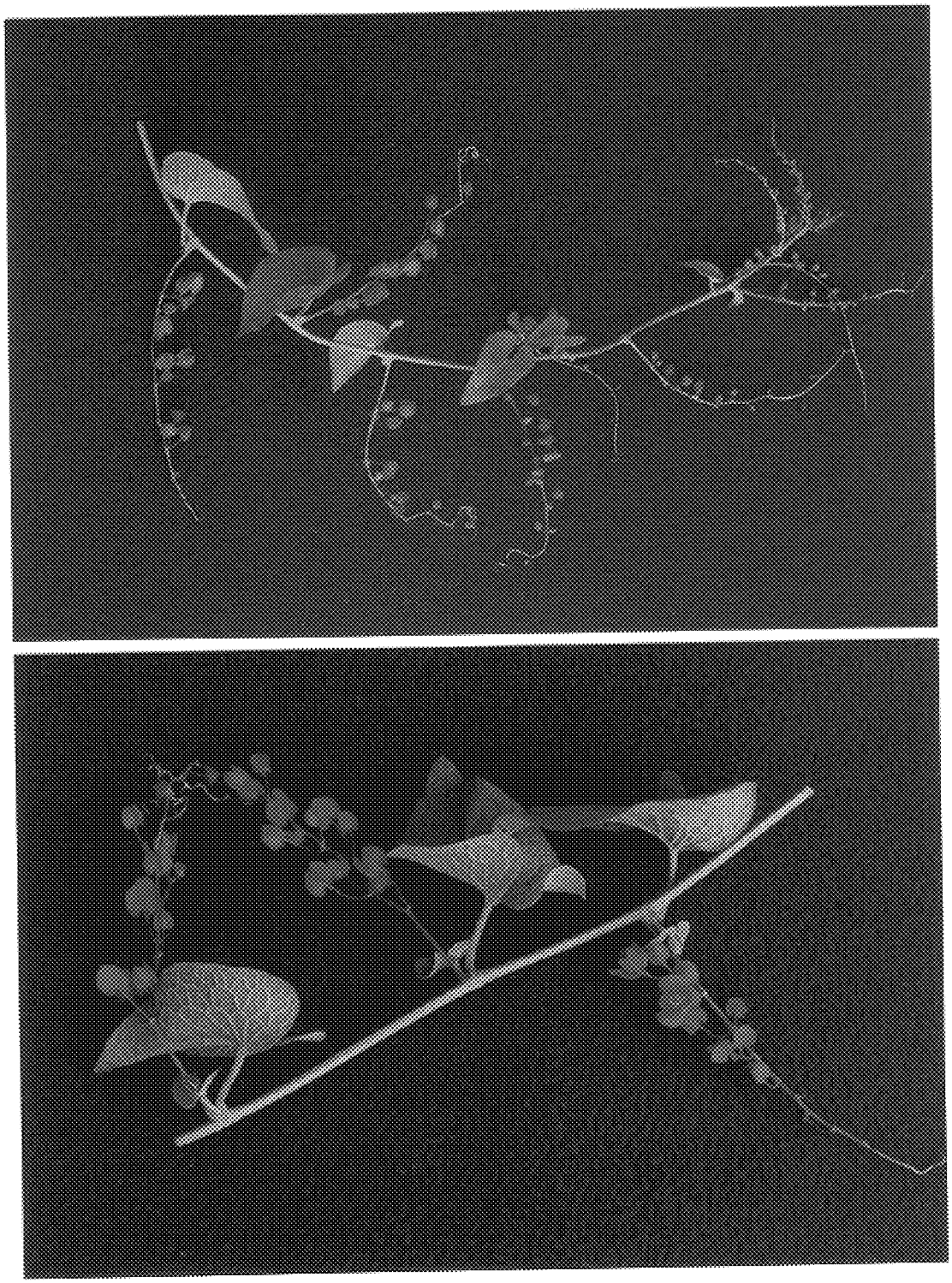

* * * * *